United States Patent [19]

Hartmeier

[11] Patent Number: 4,459,312

[45] Date of Patent: Jul. 10, 1984

[54] ENZYMES BONDED TO LIVING YEAST CELLS

[75] Inventor: Winfried Hartmeier, Ingelheim, Fed. Rep. of Germany

[73] Assignee: C. H. Boehringer Sohn, Ingelheim am Rhein, Fed. Rep. of Germany

[21] Appl. No.: 269,475

[22] Filed: Jun. 2, 1981

[30] Foreign Application Priority Data

Jun. 9, 1980 [DE] Fed. Rep. of Germany ....... 3021629

[51] Int. Cl.$^3$ ................... C12C 11/04; C12G 1/00; C12N 11/18
[52] U.S. Cl. ......................... 426/13; 426/12; 426/15; 426/16; 426/62; 435/174; 435/175; 435/181; 435/256
[58] Field of Search ............... 435/174, 175, 177, 181, 435/255, 256; 426/15, 16, 11, 62, 12, 13

[56] References Cited

U.S. PATENT DOCUMENTS

| | | | |
|---|---|---|---|
| 3,379,534 | 4/1968 | Gablinger | 426/13 |
| 3,597,219 | 8/1971 | Wildi et al. | 426/12 |
| 3,639,558 | 2/1972 | Csizmas et al. | 435/181 X |
| 3,736,231 | 5/1973 | Stanley et al. | 435/177 |
| 3,796,634 | 3/1974 | Haynes et al. | 435/177 X |
| 3,950,222 | 4/1976 | Takasaki | 435/174 |
| 4,320,194 | 3/1982 | Bull | 435/175 X |
| 4,323,650 | 4/1982 | Rosevear | 435/174 |

OTHER PUBLICATIONS

Griffith et al., A New Method for Coating Fermentation Tower Packing so as to Facilitate Microorganism Attachment, Developments in Industrial Microbiology, vol. 17, 1976, (pp. 241–246).

Hirano et al., Aminoacylase Pellets, Chem. Abstr., vol. 86: 119176c, 1977, (p. 379).

Hagerdal et al., The Production of Ethanol from Cellobiose Using Baker's Yeast Co–Immobilized with Beta-Glucosidase, Food Process Engineering, vol. 2, 1980, (pp. 129–132).

*Primary Examiner*—David M. Naff
*Attorney, Agent, or Firm*—Hammond & Littell, Weissenberger & Dippert

[57] ABSTRACT

Living, fermentable yeast cells are prepared having an enzyme or mixture of enzymes coupled thereto. Enzyme coupling is carried out by contacting at least partially dehydrated living yeast cells with an aqueous enzyme solution to cause the yeast cells to rehydrate and a layer of enzyme to form on the surface of the yeast cells, and than contacting the rehydrated yeast cells with an enzyme-precipitating solution which optionally contains a cross-linking agent to cause the enzyme to become attached to the yeast cells. An aqueous solution of tannin is preferably the enzyme-precipitating solution and gluardialdehyde is preferably the cross-linking agent. Pepsin coupled to Saccharomyces yeast, when used to ferment grape must to produce wine, results in practically foam-free attenuation, quicker fermentation and better self-clarification. Saccharomyces yeast having amgloglucosidase coupled thereto may be used to ferment beer wort to produce a diet beer.

25 Claims, 2 Drawing Figures

ENZYMES BONDED TO LIVING YEAST CELLS

FIELD OF THE INVENTION

This invention is directed to whole microbial cells co-immobilized with enzymes. More particularly, this invention is directed to enzymes coupled to living, fermentable yeast cells.

BACKGROUND OF THE INVENTION

It is well known that fermentable yeasts are used in the preparation of alcoholic beverages. The enzymes occurring in the corresponding yeasts act to break down one or more substances (for example, fermentable sugar in beer wort, grape must, or distillery mash), and to, at least partly, convert the substances into ethyl alcohol. This latter function is notable because of the use of alcohol as a semiluxury food substance, as a chemical raw material, and as fuel for combustion engines.

Unfortunately, the yeasts employed are not always sufficiently equipped with enzymes for engaging in all desired reactions. Wine yeasts, for example, possess only insufficient protein-splitting activity, so that proteins in the must are degraded only on a small scale. This may lead to a foaming over of the fermenting batches as well as to considerable clarification and stability difficulties in wines, which can only be remedied by additional application of, for example, bentonite or other fining agents such as, for example, gelatin or silicasol.

Also, it has not previously been possible to attenuate, i.e., ferment, the trisaccharide raffinose occurring in many raw materials of the distillery with the usual distilling yeasts and top-fermented brewery yeasts of the *Saccharomyces cerevisiae* type. Since α-galactosidase (melibiase) is missing in these yeasts, only one-third of the raffinose is attenuated; the remaining two-thirds of the raffinose consisting of melibiose occurring in beer wort or molasses, remains unused, so that the alcohol yield remains under its theoretically possible value.

For brewery practice with bottom and also top-fermented brewers yeasts (*Saccharomyces uvarum* and *carlsbergensis* or *Saccharomyces cerevisiae*, respectively) it is disadvantageous that these types of yeast have practically no β-glucanase by nature, so that β-glucanes are not split and cause difficulties with the subsequent filtering of the beer. Analogous conditions prevail due to the lack of pectinases in wine yeasts (*Saccharomyces cerevisiae, Saccharomyces bayanus*).

It has already been known, or has at least suggested in the prior art, to add to a fermenting batch all those enzymes which the yeast within the fermenting batch does not contain. Thus, soluble β-glucanases are used, for example, to obtain a sufficient glucane degradation in beer. In wine production soluble pectinases have already been used. These methods, however, have the disadvantage, that the finished beverage, for example, beer or wine, still contains the enzyme protein. Further shortcomings in the use of soluble enzymes include, for example, the situation such as that of soluble pepsin and its only insufficient activity in foam suppression in must attenuation.

When known immobilized enzymes are used, the final product, for example, beer or wine, may be kept free from enzyme protein; however, these preparations—when added to the fermenting batch in addition to the yeast—do not lead to the desired success of a quick degradation of the substance not degradable by the fermenting yeast if the fermentation batch is not stirred intensely by means of a stirrer. Thus, successful employment of the known immobilized preparations demands additional technical expenditure, which may cause considerable difficulties and is not practical in many applications (such as breweries, distilleries, or wine producers). Often the use of known immobilized preparations is precluded by harmful side-effects, such as, for example, undesired addition of oxygen and excessive growth of yeast.

In addition, it has already been known from works by Y. Takasaki that enzymes can be bound to cells of microorganisms. U.S. Pat. No. 3,950,220 as well as Agr. Biol. Chem., 38, 1081–1082 (1974), furnish details on the subject. The process disclosed by Takasaki is suitable for mold fungi, but it is unsuitable for fermenting yeast cells as it leads to complete inactivation of the fermenting enzyme system of the cells. Furthermore, it has the drawback that only relatively few enzyme proteins can be bound to one cell, and thus, the specific enzyme activity of these preparations is insignificant.

The above-mentioned disadvantage of a small enzyme coverage on the enzyme-cell co-immobilisates is remedied by a new method by B. Hägerdal and K. Mosbach (Abstracts for the Food Process Engineering Congress, Helsinki, 1979), where β-glucosidase in alginate gel is wrapped around the cells. This method will work with living, fermentable yeast cells; however, there is the drawback that very big enzyme yeast cell particles are formed, so that the usual floating capacity of the yeast cells in media to be attenuated (mash, wort, must, and similar ones) is diminished and considerable decreases of the fermentation output occur. A further disadvantage is the increased resistance to diffusion which the relatively thick enzyme-alginate layer provides against the passing of fermentable substances towards the yeast cell.

DETAILED DESCRIPTION OF THE INVENTION

Figure 1:
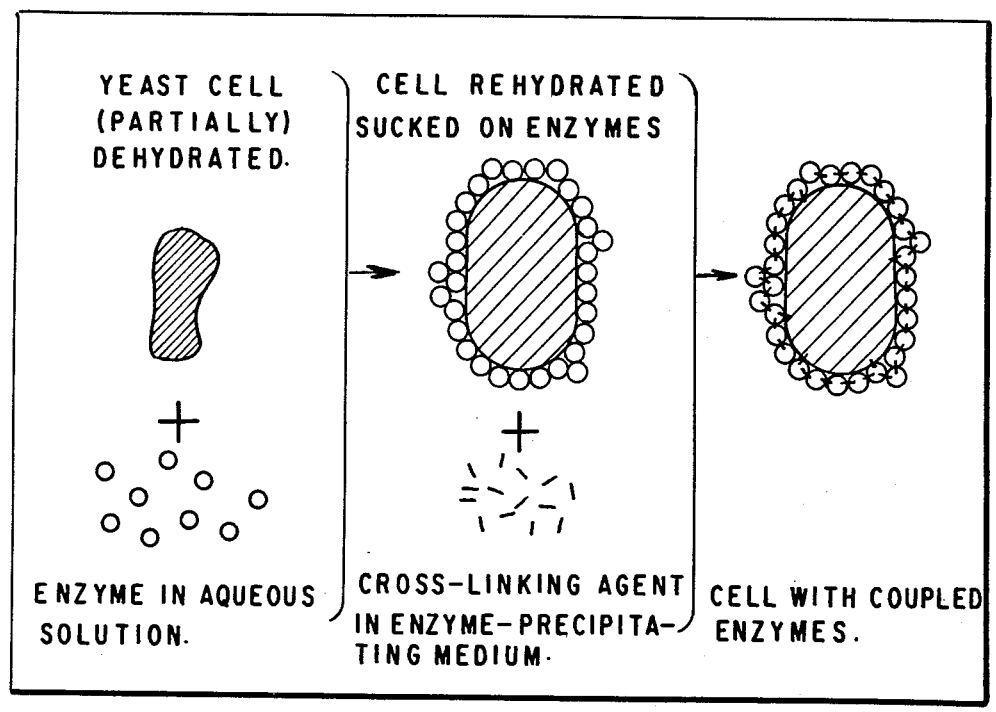
FIG. 1 is a pictoral representation of an embodiment of the invention.

It has now been found that products with technical and economic advantages result if enzymes are coupled to fermentable yeast cells while maintaining fermentability, which the corresponding yeasts do not naturally contain, or do not contain to a sufficient extent, for the desired purpose. Thus, according to the invention products are formed which are co-immobilisates from fermentable yeast cells occurring essentially as single units, that is, not in agglomerated form, and from one or several enzymes. The basic construction of such co-immobilisates, as well as the process for their product, are illustrated in FIG. 1.

According to the invention, the fermentable yeast cells, which must be dehydrated at least partially, are put into an aqueous solution with one or several enzymes intended for coupling. The yeast cells swell upon taking up water, and since the water between the yeast cells is more or less removed, the enzyme molecules remain, preferably adjacent to the surfaces of the yeast cells. Subsequently an enzyme-precipitating solution that does not inactivate fermentability of the yeast, which solution optionally contains a cross-linking agent, is added, causing the enzymes to become attached to the yeast cells, the enzyme molecules also being linked firmly to one another. The resulting cross-linked enzyme/fermentable yeast product comprises the co-immobilisate according to the invention. The addition of the enzyme-precipitating substance has the effect that the yeast cells with the surrounding enzyme layers appear to exist mostly singly and do not stick one to the other in bigger agglomerates.

The, at least, partial dehydration of the yeast cells employed may be effected—in case it does not already exist—by means of a process for production of active dry yeast known per se, such as, for example, in line with the vacuum drying process described in German Pat. No. 2,515,029, incorporated herein by reference. A further known and suitable method for an at least partial withdrawal of water from the interior of the cell is the use of substance solutions with high osmotic pressure, such as, for example, solutions of salts, sugar, or glycerin. When the cells are placed into such solutions with high osmotic value, they deliver part of their water from the interior cell into the surrounding solution. After separation of the surrounding solution, they are suitable for production of the yeast-enzyme co-immobilisate as they now represent partially dehydrated initial cell material.

According to the invention, the more or less dehydrated yeast cells are introduced into an aqueous enzyme solution. When this is done, the quantity of water of the enzyme solution is to be calculated in such a way that the yeast cells take up most of the water after their rehydration and that as little water as possible or no water remains between the cells. The required quantity of water can be determined by preliminary tests. In general about 70 to 75 percent by weight of water content in the yeast cells is reached by a complete absorption of the water. During rehydration of the yeast cells in the aqueous enzyme solutions, the enzymes are "sucked onto" the yeast cells and end up adjacent to, that is, lying upon, the yeast cell surfaces.

It is known that when the yeast cells are rehydrated (remoisturized), one must proceed very cautiously since, for example, yeast cells are generally more sensitive to cold shock during rehydration, the stronger the degree of drying is. Therefore, it is useful to carry out remoisturizing by means of an aqueous enzyme solution warmed up to approximately 30° to 40° C. If desired, the yeast cells may also be admixed with corresponding protective agents that facilitate rehydration and protect the cells from damage to their fermentability. See, for example, German Published Patent Application (DE-OS) Nos. 25 31 800 and 24 35 226.

To keep the enzyme molecules lying on the cell surfaces after rehydration of the yeast cells until the final enzyme binding or cross-linking and to avoid agglomeration of the cell particles, the addition of an enzyme-precipitating substance is required simultaneously with or before the addition of a cross-linking agent. For this purpose tannin in a from about 0.5 to 5% aqueous solution is preferably used. Organic solvents generally used for enzyme precipitation (such as, for example, aceton, i-propanol, and the like) are unsuitable because they considerably decrease the fermentability of the yeast or destory it completely. Also, such solvents exercise a strong dehydrating effect on the yeast cells which may lead to a detachment of the enzyme layer lying upon the cells.

Useful cross-linking agents that may be employed include generally known bifunctional or polyfunctional compounds such as, for example, diisocyanates, glutardialdehyde, hexamethylene diamine, and hexamethylene tetramine. Glutardialdehyde in aqueous solution in a concentration of from about 1 to 10% is preferably used in the reaction mixture. Cross-linking is carried out for from several minutes up to several days, preferably for from about 1 to 5 hours, at from about 20° to 30° C. During the cross-linking it is favorable to agitate the reaction batch slightly, for example, by stirring or shaking. When the cross-linking is finished, the resulting preparation is usually washed and is then used further in moist or, if desired, dried condition.

The following table sets forth several examples of combinations of yeast cells and enzymes according to the invention and the potential applications of such combinations:

TABLE

| Species of Yeast | Coupled Enzyme | Possibility of Use |
|---|---|---|
| Saccharomyces cerevisiae or bayanus | pepsin | wine production from musts rich in protein |
| Saccharomyces cerevisiae or bayanus | pectinase | attenuation of fruit or grape must |
| Saccharomyces cerevisiae | β-galactosidase (= lactase) | attenuation of whey and similar media containing lactose |
| Saccharomyces cerevisiae | α-amylase/amyloglucosidase | attenuation of media containing starch or dextrin |
| Saccharomyces cerevisiae | α-galactosidase | attenuation of mashes containing raffinose |
| Saccharomyces cerevisiae | cellulase/cellobiase | attentuation of mashes containing cellulose |
| Saccharomyces uvarum | papain | production of protein-stable beers |
| Saccharomyces uvarum | β-glucanase | beer production from worts rich in glucan |
| Saccharomyces uvarum | α-amylase/amyloglucosidase | production of diet beer |
| Kloeckera appiculata | pepsin | preliminary fermentation of wine must with high content of sulfite |

Particularly favorable microbial cells co-immobilized with enzymes have been the ones produced by the coupling of wine yeasts of the species Saccharomyces cerevisiae and Saccharomyces bayanus with pepsin.

Surprisingly, the co-immobilisates according to the invention make possible a practically foam-free attenuation when they are used in must rich in protein, which does not happen when the same quantity of soluble pepsin is used in conjunction with the same quantity of normal yeast. Furthermore, the use of the product according to the invention enhances fermentation, accelerates self-clarification of the wines, and decreases the amounts of agents needed for fining the wines.

The following examples are intended to illustrate the invention and should not be construed as limiting the invention thereto.

EXAMPLES

Example 1

Fourteen grams of fresh, compressed bakery yeast from the yeast factory Pleser, Darmstadt, were stirred with 1.4 gm of powdery sorbitol for 15 minutes. During this procedure, the yeast was partially dehydrated by the movement of intracellular water (from the interior of the cells) into the intercellular room (room between the cells). Then, the yeast was subjected to suction filtration and the water from the cells as well as the sorbitol added were subsequently removed. After the dehydration procedure, the yeast had a water content of only 47%, which corresponds to a dry substance content of 53%.

Apart from the dehydration batch indicated above, 0.5 gm of the commercial cellulolytic enzyme preparation "Cellulase AP3" from the firm Amano Pharmaceutical Co. Ltd., Nagoya (Japan) were dissolved with 5 ml of deionized water at room temperature. Into this enzyme solution was stirred the total quantity of the partially dehydrated compressed yeast prepared above. Stirring was continued for 15 minutes until the yeast was well rehydrated and a suspension formed. Then, the batch was warmed to 25° C. and admixed with 20 ml of 2% tannin solution and 0.1 ml of 25% glutardialdehyde solution. After addition of the glutardialdehyde, the batch was shaken in an Erlenmeyer flask for 4 hours at 25° C. Afterwards the enzyme-yeast co-immobilisate formed was washed thoroughly with water.

To determine the fermentability of the co-immobilisate, it was added to a 50 ml aqueous fermentating batch containing 1 gm of cellobiose and 0.1 gm of $KH_2PO_4$, the pH-value of which was adjusted to 5.0. The fermenting batch was warmed up to 30° C., and the $CO_2$-development was measured. The $CO_2$-development amounted to 30 ml after 1 hour, 80 ml after 2 hours, and 140 ml after 3 hours. The strong $CO_2$-development showed the good attenuation output of the co-immobilisate according to the invention with cellobiose, which is not otherwise attenuated at all by bakery yeasts.

Example 2

An amount of 0.5 liter of viscous bottom yeast of (Saccharomyces uvarum) was stirred with 100 ml of glycerin for 30 minutes. Then, the supernatent liquid was removed by suction filtration. The yeast residue formed had a water content of 49%, or a dry substance content of 51%. This pressed, partially dehydrated, moist yeast served as starting yeast for the purpose of co-immobilization with amyloglucosidase and fermentation of beer wort.

Commercial amyloglucosidase (=glucoamylase; available under the tradename "Gluczyme 8000" from Amano Pharmaceutical Co. Ltd., Nagoya, Japan), in an amount of 0.5 gm was dissolved with 5 ml of deionized water at room temperature in an Erlenmeyer flask. Into this enzyme solution were stirred 10 gm of the compressed, partially dehydrated, beer yeast prepared above. After stirring was continued for 15 minutes there were admixed 20 ml of 1% tannin solution and 0.15 ml of 25% glutardialdehyde solution. The batch was shaken for 2 hours in the Erlenmeyer flask at 25° C. Then, the enzyme-yeast co-immobilisate formed was washed with water thoroughly. Finally, the excess water was removed by suction filtration.

The apparent attentuation limit was determined by use of fresh, light finished wort from a brewery in accordance with the so-called "Normalen Methode" (Pawlowski-Schild: Die brautechnischen Untersuchungsmethoden S. 165-167, 8. Auflage, Verlag Carl, Nürnberg). When partially dehydrated beer wort was used, there was an apparent attenuation value of 80%, while when yeast co-immobilized with amyloglucosidase was used, an apparent attenuation value of 102% was obtained. Thus, the co-immobilization led to a value typical for diet beer.

Example 3

An amount of 0.5 gm of the commercial fungallactase "galantase" from Aspergillus niger (available from Tokyo Tanabe Co. Ltd., Tokyo, Japan) was dissolved with 5 ml of deionized water in an Erlenmeyer flask. Then, the solution was heated to 35° C. and 2 gm of a commercial dry bakery yeast from the firm of Dr. Oetker, Bielefeld, were stirred into it. After stirring for 15 minutes, the dry yeast was rehydrated and suspended. The yeast mass formed was cooled to 25° C. and admixed with 10 ml of 2% tannin solution, 0.05 ml of 25% glutardialdehyde solution, and 25 mg of hexamethylenetetramine. Subsequently, the whole batch was shaken for 2 hours at 25° C. in the Erlenmeyer flask within a water-batch. Afterwards, the lactase-yeast coimmobilisate formed was washed thoroughly with deionized water. In 100 ml of a 5% lactose solution, which was admixed with 0.1% of sodium citrate and adjusted to a pH of 4.5, the co-immobilisate developed at 30° C. 130 ml of $CO_2$ after 30 minutes and 210 ml of $CO_2$ after 60 minutes. Thus, the co-immobilisate proved its considerable fermentability with regard to lactose, which is not fermentable with normal bakery yeast.

Example 4

An amount of 0.5 gm of a commercial pig pepsin with 2,000 FIP-units/gm (available from Merck, Darmstadt, as Article No. 7190) was dissolved in 6 ml of deionized water. After dissolution of the pepsin, the solution was heated to 38° C., and 2 gm of commercial dry wine yeast "Irgaferm CM" (=commercial product of the applicant) was stirred into it. After stirring for 15 minutes the dry yeast was rehydrated free of clots. The viscous yeast mass was cooled to 25° C. and admixed with 20 ml of 1% tannin solution and 0.1 ml of 25% glutardialdehyde solution. The whole batch was shaken in the Erlenmeyer flask for 2 hours at 25° C. Then, the pepsin-wine yeast co-immobilisate formed was washed thoroughly with tap water.

The total quantity of the pepsin-wine yeast co-immobilisate described was added to 10 liters of fresh Silvaner grape must at 20° C. to start fermentation. Parallel thereto, 2 gm of dry wine yeast "Irgaferm"—not co-immobilized with pepsin—were added, after rehydration, at 38° C. to 10 liters of the same Silvaner grape must. It was found that fermentation with the co-immobilisate according to the invention even in it most intense phase never formed a layer of foam of more than 1 cm, while the foam layer of the control almost reached the volume of the fermentation liquid.

Figure 2:
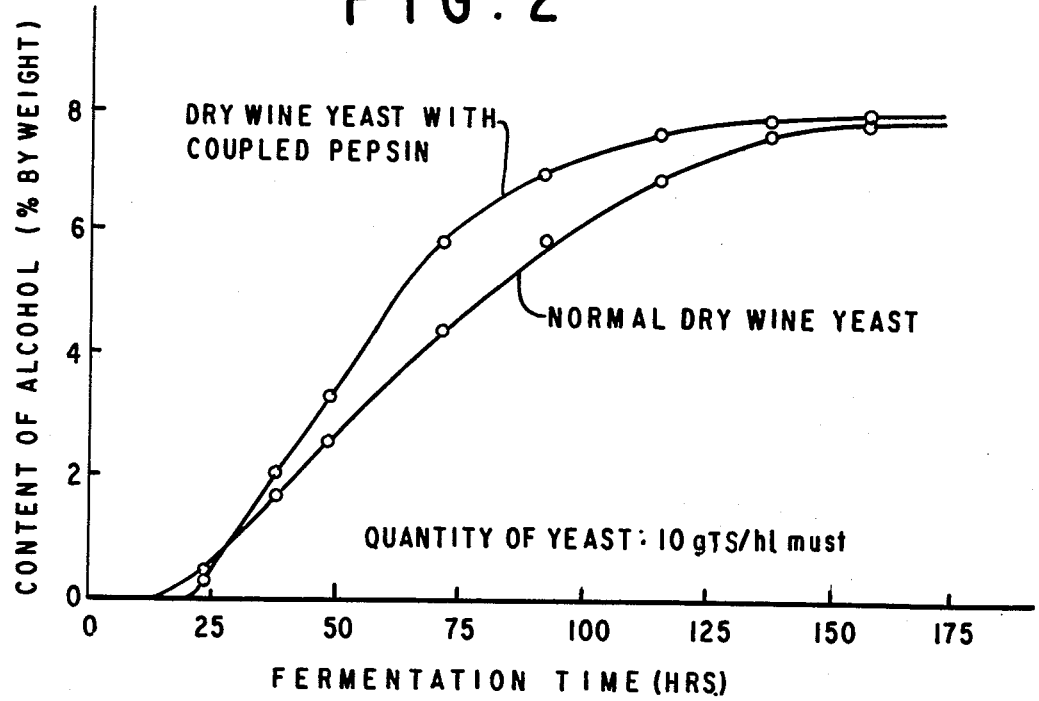
FIG. 2 sets forth a portion of the results obtained in Example 4.

A further advantage of the co-immobilisate according to the invention was the quicker fermentation of the must. The rates of fermentation are set forth in the graphical representation of FIG. 2, where the rate of fermentation—as reflected by the alcohol content of the fermentation batch, which content was determined by known procedure—is plotted as a function of time.

Furthermore, when the product according to the invention was added, a better self-clarification of the wine was observed and a protein-stable wine was gained without further fining (for example, by bentonite, gelatin, or silicasol). The better self-clarification showed clearly when both the filtered wine samples were heated for 24 hours to 60° C. and then cooled down to 20° C. again. The wine produced with the product according to the invention remained completely clear during this treatment while the control wine showed strong turbidity.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A process for the preparation of a water-insoluble co-immobilized enzyme comprising living, fermentable yeast cells having an enzyme or a mixture of enzymes bonded thereto, said process comprising the steps of:
   (a) at least partially dehydrating living, fermentable yeast cells by substantially removing water from within the living yeast cells to produce dehydrated living yeast cells;
   (b) contacting the dehydrated living yeast cells from step (a) with an aqueous solution of an enzyme or mixture of enzymes to cause the living yeast cells to rehydrate and the enzyme or mixture of enzymes to form layers upon the surfaces of the living yeast cells; and
   (c) contacting the rehydrated living yeast cells from step (b) with an enzyme-precipitating substance other than an enzyme-precipitating organic solvent and with a cross-linking agent to obtain living yeast cells having said enzyme or mixture of enzymes bonded thereto, said contacting with said enzyme-precipitating substance being carried out simultaneously with or before contacting with said cross-linking agent.

2. The process of claim 1, wherein the yeast is *Saccharomycetes cerevisiae* or *Saccharomycetes bayanus*.

3. The process of claim 1, wherein the enzyme is pepsin.

4. The process of claim 1, wherein the aqueous solution contains water in an amount that is entirely or almost entirely absorbed by the dehydrated yeast cells.

5. The process of claim 1, wherein the yeast cells reach a water saturation content of from about 70 to 75 percent by weight during rehydration.

6. The process of claim 1, wherein the aqueous enzyme solution is heated to from about 30° to 40° C.

7. The process of claim 1, wherein the step (b) a suspension or a slurry is formed.

8. The process of claim 1, wherein the enzyme precipitating medium comprises an aqueous solution of tannin.

9. The process of claim 8, wherein the aqueous solution contains from 0.5 to 5 percent of tannin.

10. The process of claim 1, wherein the cross-linking agent is glutardialdehyde.

11. The process of claim 10, wherein the aqueous solution contains from about 1 to 10 percent of glutardialdehyde.

12. A water-insoluble co-immobilized enzyme comprising living, fermentable yeast cells having an enzyme or a mixture of enzymes bonded thereto, which is prepared by the steps of:
   (a) at least partially dehydrating living, fermentable yeast cells by substantially removing water from within the living yeast cells to produce dehydrated living yeast cells;
   (b) contacting the dehydrated living yeast cells from step (a) with an aqueous solution of an enzyme or mixture of enzymes to cause the living yeast cells to rehydrate and the enzyme or mixture of enzymes to form layers upon the surfaces of the living yeast cells; and
   (c) contacting the rehydrated living yeast cells from step (b) with an enzyme-precipitating substance other than an enzyme-precipitating organic solvent and with a cross-linking agent to obtain living yeast cells having said enzyme or mixture of enzymes bonded thereto, said contacting with said enzyme-precipitating substance being carried out simultaneously with or before contacting with said cross-linking agent.

13. The composition of claim 12, wherein the cross-linking agent is glutardialdehyde.

14. The composition of claim 12, wherein a mixture of enzymes is bonded to the yeast cells.

15. The composition of claim 12, wherein the yeast is *Saccharomycetes cerevisiae* or *Saccharomycetes bayanus*.

16. The composition of claim 12, wherein the enzyme is pepsin.

17. The composition of claim 12, wherein substantially each yeast cell has an enzyme coating bonded thereto.

18. The composition of claim 17, wherein from about 75 to 100 percent of the yeast cells have an enzyme coating bonded thereto.

19. In a process of preparing an alcoholic beverage from a fermentable mixture containing yeast cells, the improvement which comprises using the water-insoluble co-immobilized enzyme of claim 12.

20. The process of claim 19, wherein the cross-linking agent is glutardialdehyde.

21. The process of claim 19, wherein a mixture of enzymes is bonded to the yeast cells.

22. The process of claim 19, wherein the yeast is *Saccharomycetes cerevisiae* or *Saccharomycetes bayanus*.

23. The process of claim 19, wherein the enzyme is pepsin.

24. The process of claim 19, wherein substantially each yeast cell has an enzyme coating bonded thereto.

25. The process of claim 24, wherein from about 75 to 100 percent of the yeast cells have an enzyme coating bonded thereto.

* * * * *

UNITED STATES PATENT AND TRADEMARK OFFICE
CERTIFICATE OF CORRECTION

PATENT NO. : 4,459,312

DATED : July 10, 1984

INVENTOR(S) : WINFRIED HARTMEIER

It is certified that error appears in the above-identified patent and that said Letters Patent is hereby corrected as shown below:

Column 3, line 67, "destory" should read -- destroy --.

Column 6, line 50, "it" should read -- its --.

Column 7, line 1 of claim 7, "wherein the" should read -- wherein in --.

Signed and Sealed this

Fifteenth Day of January 1985

[SEAL]

*Attest:*

GERALD J. MOSSINGHOFF

*Attesting Officer*  *Commissioner of Patents and Trademarks*